United States Patent [19]

Sugimori et al.

[11] Patent Number: 4,592,857

[45] Date of Patent: Jun. 3, 1986

[54] 2,3-DICYANO-5-SUBSTITUTED PYRAZINES

[75] Inventors: Shigeru Sugimori, Fujisawashi; Yasuyuki Goto, Yokohamashi, both of Japan

[73] Assignee: Chisso Corporation, Osaka, Japan

[21] Appl. No.: 641,730

[22] Filed: Aug. 17, 1984

[30] Foreign Application Priority Data

Aug. 22, 1983 [JP] Japan .................................. 58-152892
Oct. 17, 1983 [JP] Japan .................................. 58-193839

[51] Int. Cl.⁴ .......................... C09K 3/34; G02F 1/13; C09D 241/00; C09D 241/02
[52] U.S. Cl. ............................. 252/299.61; 252/299.5; 350/346; 350/350 R; 544/336; 544/408
[58] Field of Search ................ 544/336, 408; 252/299.61, 299.5; 350/346, 350 R

[56] References Cited

U.S. PATENT DOCUMENTS

| | | | |
|---|---|---|---|
| 3,997,536 | 12/1976 | Boller et al. | 252/299.61 |
| 4,273,929 | 6/1981 | Boller et al. | 252/299.61 |
| 4,279,770 | 7/1981 | Inukai et al. | 252/299.63 |
| 4,311,610 | 1/1982 | Zaschke et al. | 252/299.61 |
| 4,452,718 | 6/1984 | Schadt et al. | 252/299.61 |
| 4,479,885 | 10/1984 | Mukoh et al. | 252/299.62 |

FOREIGN PATENT DOCUMENTS

| | | | |
|---|---|---|---|
| 56501 | 7/1982 | European Pat. Off. | 252/299.61 |
| 84194 | 7/1983 | European Pat. Off. | 252/299.61 |
| 2257588 | 6/1973 | Fed. Rep. of Germany | 252/299.61 |
| 2854603 | 7/1979 | Fed. Rep. of Germany | 544/336 |
| 3209178 | 9/1983 | Fed. Rep. of Germany | 252/299.61 |
| 54-11887 | 1/1979 | Japan | 252/299.61 |
| 54-41285 | 4/1979 | Japan | 252/299.61 |
| 55-22609 | 2/1980 | Japan | 252/299.61 |
| 57-14581 | 1/1982 | Japan | 544/336 |
| 58-121272 | 7/1983 | Japan | 252/299.61 |
| 2049692 | 12/1980 | United Kingdom | 252/299.61 |

OTHER PUBLICATIONS

C.A., vol. 89, 163542e (1978).
C.A., vol. 96, 68939a (1982).
C.A., vol. 89, 109366n (1978).
C.A., vol. 92, 94433t (1980).
Demus, D., et al., Flussice Kristalle in Tabellen, pp. 263–266 (1974).
Osman, M., et al., Mol. Cryst. Liq. Cryst., vol. 82 (Lett.), pp. 331–338 (1983).
"Synthesis of New Pyrazine Compounds from Diaminomaleonitrile" *Chemical Abstracts*, 89:163542e, Tsuda et al. (1978).
"Synthesis and Mesomorphic Properties of Diphenyl- and Biphenylylpyrimidines", *Zeitschrift fur Naturforschung*, 33B, 433–438 (1978), Boller et al.

Primary Examiner—Teddy S. Gron
Attorney, Agent, or Firm—Leydig, Voit & Mayer, Ltd.

[57] ABSTRACT

Novel liquid crystal compounds having a positive dielectric anisotropy and liquid crystal compositions containing the same are provided, which liquid crystal compounds are 2,3-dicyano-5-substituted pyrazines expressed by the general formula

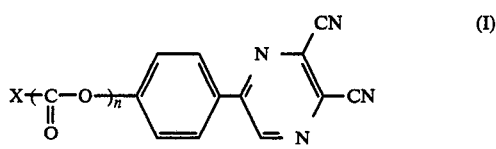

wherein n represents 0 or 1; X represents R,

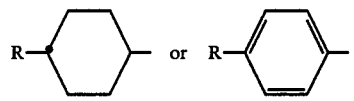

in the case of n=0 and R,

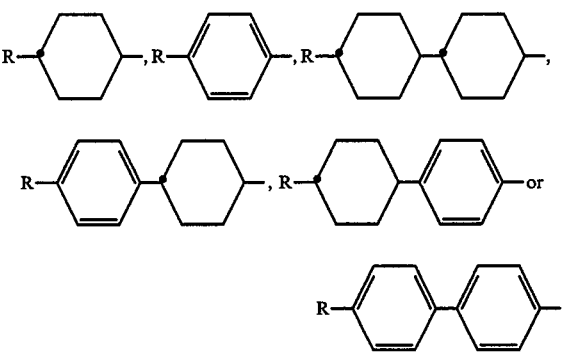

in the case of n=1; and R represents a linear chain alkyl group or an alkoxy group, each of 1 to 10 carbon atoms, and which liquid crystal compositions, when sealed in a TN cell, make it possible to operate the cell under a low threshold voltage and in a small consumption of electric power.

22 Claims, No Drawings

2,3-DICYANO-5-SUBSTITUTED PYRAZINES

BACKGROUND OF THE INVENTION

1. Field of the Invention

This invention relates to novel organic compounds, and more particularly it relates to novel liquid crystal compounds having a positive dielectric anisotropy, novel organic compounds useful as a component of liquid crystal compositions and liquid crystal compositions containing these novel compounds.

2. Description of the Prior Art

Liquid crystal substances having a positive dielectric anisotropy are not only utilizable for liquid crystal display elements using nematic liquid crystals of a twisted arrangement, i.e. the so-called TN type cells, but also utilized for color liquid crystal display elements having a guest-host effect applied by adding a suitable dyestuff. As for these liquid crystal materials, there is no compound which is singly endurable to practical use in respect of their various performances such as mesomorphic range, operation voltage, response performance, etc. Thus, actually it is the present status that several kinds of liquid crystal compounds or non-liquid crystal compounds are mixed to obtain compositions endurable to practical use.

The object of the present invention is that in a liquid crystal display device wherein a nematic liquid crystal material having a positive dielectric anisotropy is used, a component constituting the nematic liquid crystal material by which the device can be operated under a low threshold voltage and in a small consumption of electric power is provided.

We have made extensive research for compounds satisfying the above object and as a result have found novel compounds having a dicyanopyrazine group.

SUMMARY OF THE INVENTION

A first aspect of the present invention resides in:

(1) 2,3-dicyano-5-substituted pyrazines expressed by the general formula

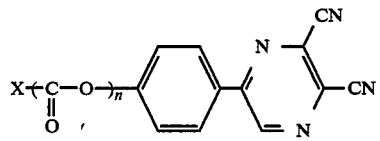

wherein n represents 0 or 1; X represents R,

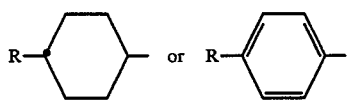

in the case of n=0 and R,

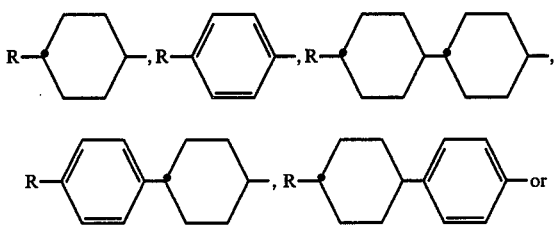

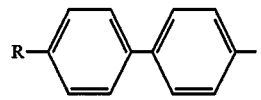

in the case of n=1; and R represents a linear chain alkyl group or an alkoxy group, each of 1 to 10 carbon atoms; and as embodiments of the above item (1), (2) 2,3-dicyano-5-(p-substituted phenyl)pyrazines expressed by the general formula

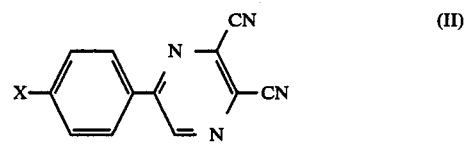

wherein X represents R,

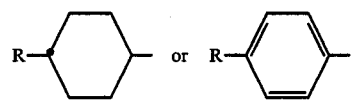

and R represents a linear chain alkyl group or an alkoxy group, each of 1 to 9 carbon atoms; and (3) substituted monocarboxylic acid esters or carbonic acid esters of p-(2,3-dicyanopyrazinyl-5)phenol expressed by the general formula

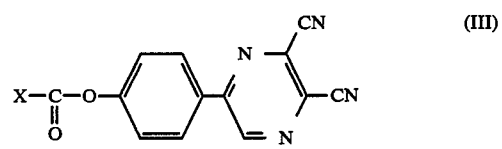

wherein X represents R,

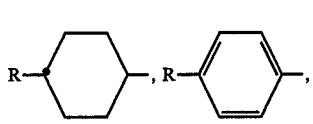

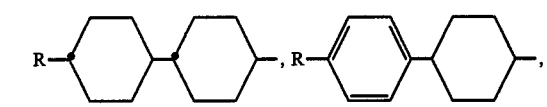

and R represents a linear chain alkyl group or an alkoxy group, each of 1 to 9 carbon atoms.

A second aspect of the present invention resides in:

(4) A liquid crystal composition comprising at least one kind of 2,3-dicyano-5-substituted pyrazine expressed by the general formula (I) used in an amount effective to enhance liquid crystal properties of the above item (1).

DESCRIPTION OF THE PREFERRED EMBODIMENTS

The compounds of the present invention include those having a liquid crystal phase and those exhibiting no liquid crystal phase, and either are preferably used as a component for liquid crystal materials. Most of the former compounds have a broad nematic temperature range, but since they have high crystalline-nematic transition points, they cannot be singly used as a material for display elements.

However, since they have a superior compatibility with other liquid crystal compounds and also a high nematic-clearing point, mixing thereof with one kind of or a mixture of several kinds of other liquid crystal substances such as those having a Schiff base group, azoxy group, benzoic acid phenyl ester group, cyclohexanecarboxylic acid phenyl ester group, biphenyl group, phenylcyclohexane group, phenylpyrimidine group, phenylmetadioxane group, etc., elevates the clearing points of these other compounds; hence they are useful as the so-called high temperature liquid crystal component. Further, since they have a larger dielectric anisotropy value (Δε) than those of liquid crystal substances such as those of cyanoterphenyl group, cyanobiphenylylcyclohexane group, etc. which have so far been broadly used for the same purpose, use of the compounds of the present invention makes it possible to reduce the driving voltage of the liquid crystal display device to a large extent even when they are used in a small amount.

Further the latter compounds exhibiting no liquid crystal phase also have a superior compatibility with the above-mentioned other liquid crystal compounds, and when they are added to liquid crystal compositions, it is possible to reduce the driving voltage of a liquid crystal display device wherein such liquid crystal materials are used, and further it is possible to improve the steepness on a curve of percentage transmission/impressed voltage of the display device.

The compounds of the present invention having such superior specific features can be prepared according to the following reaction:

(i) In the case of n=0,

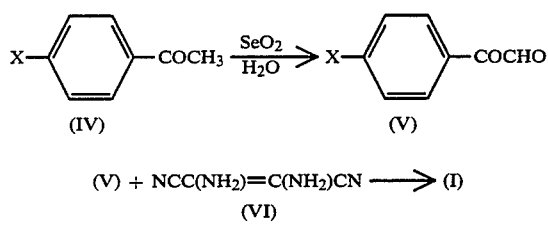

An oxidizing agent such as selenium dioxide is first reacted with a 4-substituted acetophenone (IV) to obtain a 4-substituted phenylglyoxal (V). (V) and diaminomaleonitrile (VI) are then subjected to a condensation reaction in the presence of an acid catalyst such as sulfuric acid, p-toluene sulfonic acid, hydrochloric acid, etc. Water formed during the condensation reaction is removed in the form of an azeotropic mixture thereof with an inert organic solvent such as benzene, toluene, xylene, etc. The reaction product is subjected to a series of purification treatments of extraction with solvent, washing with water and recrystallization to isolate the objective compound of the formula (I).

(ii) In the case of n=1,

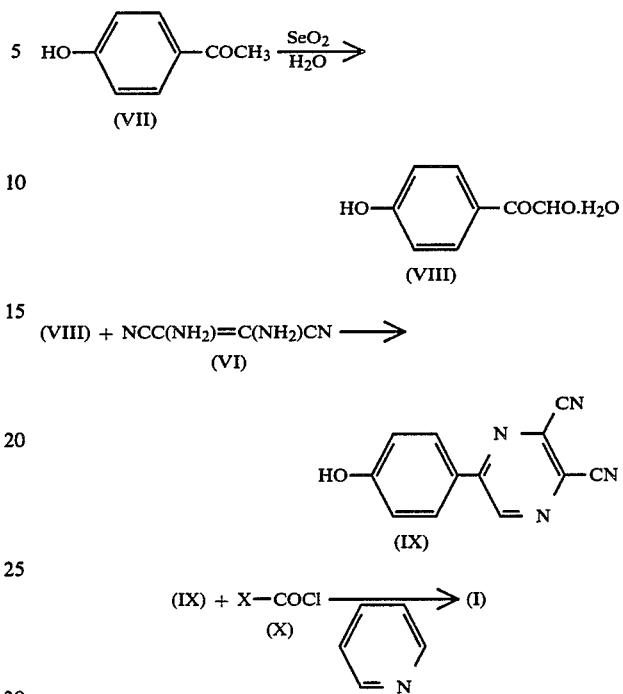

In the same manner as above, selenium dioxide is reacted with 4-hydroxyacetophenone (VII) to obtain 4-hydroxyphenylglyoxal hydrate (VIII), which is reacted with diaminomaleonitrile (VI) to obtain a phenol derivative (IX), which is then reacted with a corresponding carboxylic acid chloride in the presence of pyridine to obtain the objective compound (I).

The preparation of the compounds of the present invention and the examples of their use will be described in more details by way of Examples.

In these Examples, crystalline-nematic transition point, nematic-clearing point and crystalline-clearing point are abbreviated to C-N point, N-I point and C-I point, respectively.

EXAMPLE 1

2,3-Dicyano-5-(4-propylphenyl)pyrazine

Selenium dioxide (11.1 g, 0.1 mol) was added to a mixed solution of p-dioxane (60 ml) and water (2 ml) and dissolved therein on heating at 60° C., followed by adding 4-propylacetophenone (16.2 g, 0.1 mol) all at once, reacting the mixture on heating under reflux for 4 hours, filtering off an inorganic material deposited after completion of the reaction, distilling off p-dioxane from the filtrate, and distilling a remaining oily substance under reduced pressure to obtain 4-propylphenylglyoxal (13.0 g).

B.P.: 85°~88° C./2 mmHg.

This 4-propylphenylglyoxal (8.0 g, 0.05 mol) and diaminomaleonitrile (5.4 g, 0.05 mol) were dissolved in benzene (50 ml), followed by adding p-toluenesulfonic acid (0.05 g) to the solution, reacting them on heating under reflux for 3 hours, while distilling off water formed, allowing the reaction liquid to cool down to room temperature after completion of the reaction, adding water (50 ml), separating the resulting two layers, twice washing the benzene solution with 5% sodium bicarbonate solution (50 ml), further washing it with water, drying it with anhydrous sodium sulfate, distilling off benzene from the solution, and recrystallizing a remaining solid material from ethanol (10 ml) to obtain the objective product (8.9 g).

M.p.: 87.0°~87.9° C.

EXAMPLE 2

4-(2,3-dicyanopyrazinyl-5)phenyl 4-(trans-4-propylcyclohexyl)benzoate (1) Preparation of 4-hydroxyphenylglyoxal hydrate Selenium dioxide (11.1 g, 0.1 mol) was added to a mixed solution of p-dioxane (60 cc) and water (2 cc) and dissolved therein on heating at 60° C., followed by adding 4-hydroxyacetophenone (13.6 g, 0.1 mol) all at once, reacting the mixture on heating under reflux for 4 hours, filtering off an inorganic material deposited after completion of the reaction, distilling off p-dioxane from the filtrate, adding water (80 cc) to the resulting red-brown oily material, heating the mixture with stirring at 80° C. for 2 hours, allowing the reaction liquid to cool down to room temperature after completion of the reaction, and filtering off and drying deposited crystals to obtain the objective product (10.7 g). M.p.: 109°~111° C.

(2) Preparation of 4-(2,3-dicyanopyrazinyl-5)phenol

4-Hydroxyphenylglyoxal hydrate (8.6 g, 0.057 mol) obtained in the above preparation (1) and dicyanomaleonitrile (6.2 g, 0.057 mol) were dissolved in tetrahydrofuran (20 cc), and the solution was agitated at room temperature for 6 hours. After completion of the reaction, tetrahydrofuran was distilled off from the reaction mixture and a remaining solid material was recrystallized from ethanol (50 cc) to obtain the objective product (7.7 g). M.p.: 204°~205° C.

(3) Preparation of 4-(2,3-dicyanopyrazinyl-5)phenyl 4-(trans-4-propylcyclohexyl)benzoate Thionyl chloride (2 g) was added to 4-(trans-4-propylcyclohexyl)benzoic acid (1 g) and the mixture was reacted under reflux for 2 hours. After completion of the reaction, excess thionyl chloride was distilled off to obtain an acid chloride, which was added to a solution obtained by dissolving 4-(2,3-dicyanopyrazinyl-5)phenol (1 g) prepared above in the above preparation (2) in dry pyridine (3 cc), and the mixture was reacted on heating at 60° C. for 3 hours. After completion of the reaction, the reaction material was fed to water (100 cc), followed by extracting deposited crystals with toluene (10 cc), washing the extraction liquid with dilute hydrochloric acid, dilute NaOH aqueous solution and then water, drying the toluene layer over anhydrous sodium sulfate, successively distilling off toluene and recrystallizing a remaining solid material from benzene (3 cc) to obtain the objective product (1.1 g).

C-N point: 164.8~165.3; N-I point: 273° C.

EXAMPLES 3~16

Compounds shown as Examples 3~16 in Table 1 were prepared as in Examples 1 and 2. The results are shown in Table 1 together with those of Examples 1 and 2.

TABLE 1

| Example | In formula (I) n | In formula (I) X | Phase transition point (°C.) C | N | I |
|---|---|---|---|---|---|
| 1 | 0 | n-C3H7— | · 87.0–87.9 | | · |
| 2 | 1 | n-C3H7—(cyclohexyl)—(phenyl)— | · 164.8–165.3 | · 273.0 | · |
| 3 | 0 | n-C4H9— | · 81.5–82.3 | | · |
| 4 | 0 | n-C4H9O— | · 141.8–142.2 | | · |
| 5 | 0 | n-C5H11O— | · 111.3–112.0 | | · |
| 6 | 0 | n-C9H19— | · 54.6–55.1 | | · |
| 7 | 0 | n-C3H7—(cyclohexyl)— | · 100.3–100.8 | [· 23.0–23.3] | · |
| 8 | 0 | s-C5H11—(cyclohexyl)— | · 113.0–113.7 | [· 37.0–37.4] | · |
| 9 | 1 | n-C4H9—(phenyl)— | · 122.5–123.0 | | · |
| 10 | 1 | n-C5H11O—(phenyl)— | · 126.4–127.2 | [· 123.5–123.8] | · |
| 11 | 1 | n-C3H7—(cyclohexyl)—(cyclohexyl)— | · 165.7–166.9 | · 277.8–278.1 | · |
| 12 | 1 | n-C4H9O— | · 99.4–100.0 | | · |
| 13 | 1 | n-C4H9— | · 99.6–100.5 | | · |
| 14 | 1 | n-C3H7—(cyclohexyl)— | · 109.6–110.5 | · 126.4–127.5 | · |
| 15 | 1 | n-C4H9—(phenyl)—(cyclohexyl)— | · 142.1–142.5 | · 207.2–208.3 | · |
| 16 | 1 | n-C5H11—(phenyl)—(phenyl)— | · 152.5–153.1 | · 264.0–265.5 | · |

In Table 1, C, N and I in the column of phase transition point represent the respective phases of crystalline, nematic and isotropic liquids; the symbol . in the lower column represents the presence of the above respective phases; and [ ] represents a monotropic transition point.

USE EXAMPLE 1

A nematic liquid crystal composition (A) consisting of

| | |
|---|---|
| $C_2H_5$—(phenyl)—(phenyl)—CN | 8 parts by weight |
| $C_5H_{11}$—(phenyl)—(phenyl)—CN | 40 parts by weight |
| $C_7H_{15}$—(phenyl)—(phenyl)—CN | 25 parts by weight |
| $C_8H_{17}O$—(phenyl)—(phenyl)—CN | 16 parts by weight |
| $C_5H_{11}$—(phenyl)—(phenyl)—(phenyl)—CN | 11 parts by weight | has a nematic-clearing point of 63° C. A TN type display element was prepared using the above composition to observe the dependency of the transmittance upon impressed voltage. When the transmittance reaches 10% of its saturation value, the voltage $V_{10}$ at that time is defined as threshold voltage, and when the transmittance reaches 50% or 90% of its saturation value, the voltages at these times are named as $V_{50}$ or $V_{90}$; and the results of measurement of these voltages are shown in Control examples of Table 2. Next, to 95% by weight of this liquid crystal composition (A) was added 5% by weight of the compound of the present invention prepared in Example 1 to prepare a liquid crystal composition, which was similarly subjected to measurements of its clearing point and the $V_{10}$, $V_{50}$ and $V_{90}$ of a display element prepared using it. The results are shown in Table 2.

Further, for comparison, compounds which have so far been used as a driving voltage-reducing agent were added in an amount of 5% by weight to the liquid crystal composition (A), and the characteristics of display elements prepared from the blends were measured. The results are shown in Table 2.

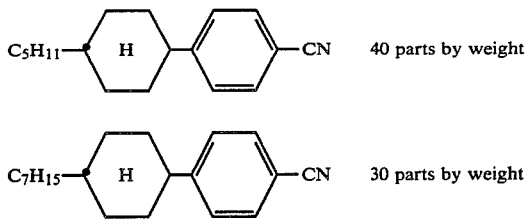

has a nematic temperature range of −5°∼52° C. This liquid crystal composition was sealed in a TN cell having a cell thickness of 10 μm. The operating threshold voltage and saturation voltage of the resulting cell were 1.54 V and 2.13 V, respectively. Further its viscosity at 20° C. was 23.5 cp.

When 5 parts by weight of 4-(2,3-dicyanopyrazinyl-5)phenyl 4-(trans-4-propylcyclohexyl)benzoate as one of the compounds of the present invention, shown in Example 2, were added to 95 parts by weight of the above liquid crystal composition, the resulting liquid

TABLE 2

| Additive | | N-I point (°C.) | $V_{10}$ (V) | $V_{50}$ (V) | $V_{90}$ (V) | $V_{50}/V_{10}$ |
|---|---|---|---|---|---|---|
| Use example 1 | 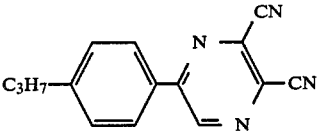 | 52.1 | 1.23 | 1.40 | 1.90 | 1.14 |
| Control example | — | 63.3 | 1.57 | 1.85 | 2.20 | 1.18 |
| Compar. ex. 1 | 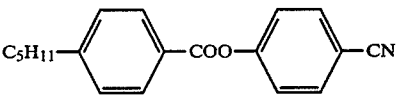 | 62.6 | 1.48 | 1.76 | 2.11 | 1.19 |
| Compar. ex. 2 | 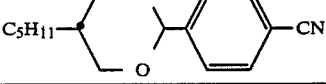 | 62.0 | 1.47 | 1.73 | 2.07 | 1.18 |

As seen from Table 2, when the compound of the present invention is added in only an amount of 5% by weight, it is possible to reduce the threshold voltage by a value as large as 0.34 V; hence the compound is not inferior to voltage-reducing agents which have so far been used.

In Table 2, "$V_{50}/V_{10}$" represents the steepness of the curve of percentage transmission/impressed voltage, and the fact that the value is close to 1 indicates that when the compound of the present invention is added, there is obtained a liquid crystal composition suitable even for the case where display elements are operated by dynamic drive.

USE EXAMPLE 2

A liquid crystal composition consisting of

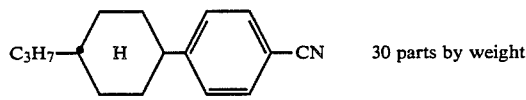 30 parts by weight crystal composition had a nematic mesomorphic range of −5°∼59° C. This composition was sealed in the same TN cell having a cell thickness of 10 μm as above. The operating threshold voltage and saturation voltage of the resulting cell were improved to a large extent, that is, down to 1.20 V and 1.82 V, respectively. Further its viscosity at 20° C. was 25 cp.

What we claim is:

1. A 2,3-dicyano-5-substituted pyrazine expressed by the formula:

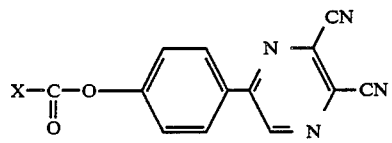

wherein X represents R—,

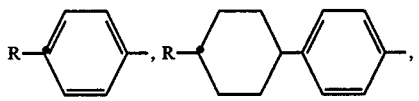,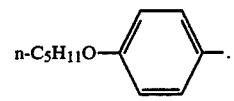

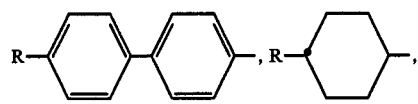,

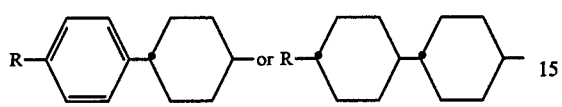

and R represents a linear chain alkyl group or an alkyloxy group, each of 1 to 10 carbon atoms.

2. The 2,3-dicyano-5-substituted pyrazine according to claim 1 wherein X represents

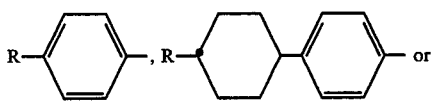 or

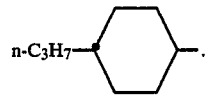.

3. The 2,3-dicyano-5-substituted pyrazine according to claim 1 wherein X represents

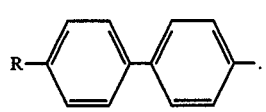 or

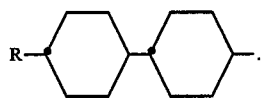.

4. The 2,3-dicyano-5-substituted pyrazine according to claim 1 wherein X is

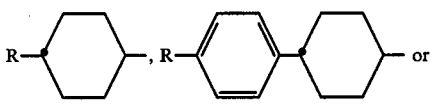.

5. The 2,3-dicyano-5-substituted pyrazine according to claim 1 wherein X is

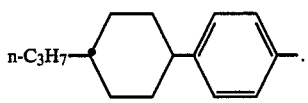.

6. The 2,3-dicyano-5-substituted pyrazine according to claim 1 wherein X is

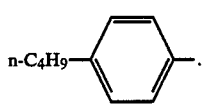.

7. The 2,3-dicyano-5-substituted pyrazine according to claim 1 wherein X is

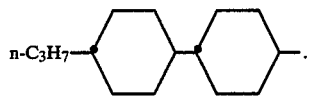.

8. The 2,3-dicyano-5-substituted pyrazine according to claim 1 wherein X is n-C$_4$H$_9$O—.

9. The 2,3-dicyano-5-substituted pyrazine according to claim 1 wherein X is n-C$_4$H$_9$—.

10. The 2,3-dicyano-5-substituted pyrazine according to claim 1 wherein X is

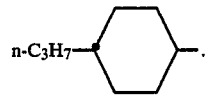.

11. The 2,3-dicyano-5-substituted pyrazine according to claim 1 wherein X is

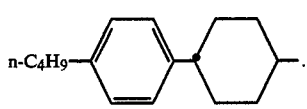.

12. The 2,3-dicyano-5-substituted pyrazine according to claim 1 wherein X is

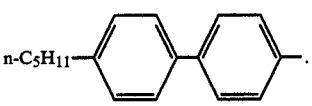.

13. A liquid crystal composition comprising at least one first substance having liquid crystal properties and at least one second substance having the formula:

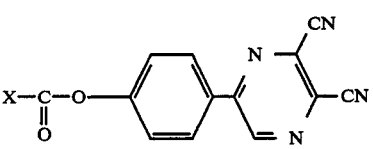

wherein X represents R—,

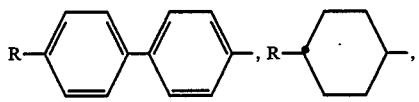

-continued

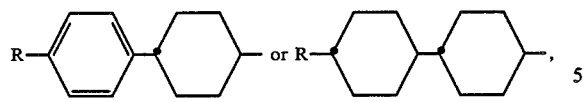

said at least one second substance present in an amount effective to enhance said liquid crystal properties.

14. The liquid crystal composition according to claim 13 wherein X is

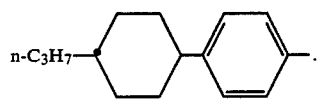

15. The liquid crystal composition according to claim 13 wherein X is

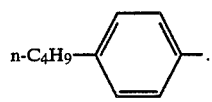

16. The liquid crystal composition according to claim 13 wherein X is

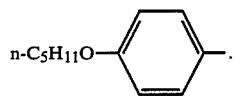

17. The liquid crystal composition according to claim 13 wherein X is

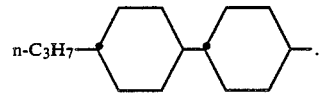

18. The liquid crystal composition according to claim 13 wherein X is n-C$_4$H$_9$O—.

19. The liquid crystal composition according to claim 13 wherein X is n-C$_4$H$_9$—.

20. The liquid crystal composition according to claim 13 wherein X is

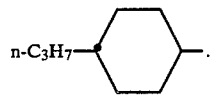

21. The liquid crystal composition according to claim 13 wherein X is

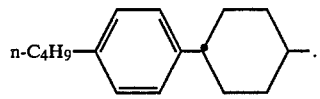

22. The liquid crystal composition according to claim 13 wherein X is

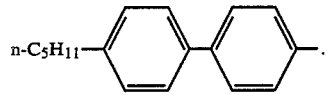

* * * * *